United States Patent [19]

Bragg

[11] Patent Number: 4,493,774

[45] Date of Patent: Jan. 15, 1985

[54] METHOD FOR IMPROVING INJECTIVITIES OF BIOPOLYMER SOLUTIONS

[75] Inventor: James R. Bragg, Houston, Tex.

[73] Assignee: Exxon Production Research Co., Houston, Tex.

[21] Appl. No.: 349,951

[22] Filed: Feb. 18, 1982

[51] Int. Cl.³ .............................................. C09K 3/00
[52] U.S. Cl. ............................. 252/8.55 D; 166/246; 166/275
[58] Field of Search ............... 252/8.55 D; 166/274, 166/275, 246

[56] References Cited

U.S. PATENT DOCUMENTS

| | | | |
|---|---|---|---|
| 3,842,909 | 10/1974 | Rhudy et al. | 166/274 |
| 4,105,461 | 8/1978 | Racciato | 252/8.5 C |
| 4,232,739 | 11/1980 | Franklin | 252/8.55 D |
| 4,234,433 | 11/1980 | Rhudy et al. | 252/8.55 D |
| 4,237,018 | 12/1980 | Schievelbein | 252/8.55 D |
| 4,271,907 | 6/1981 | Gale | 252/8.55 D |
| 4,293,428 | 10/1981 | Gale et al. | 252/8.55 D |
| 4,329,448 | 5/1982 | Cox et al. | 252/8.554 |

*Primary Examiner*—Ben R. Padgett
*Assistant Examiner*—Howard J. Locker
*Attorney, Agent, or Firm*—Michael A. Nametz; Karen T. Burleson

[57] ABSTRACT

An aqueous heteropolysaccharide solution is treated to improve its injectivity into a subterranean hydrocarbon reservoir by passing the solution through a colloid mill.

18 Claims, No Drawings

METHOD FOR IMPROVING INJECTIVITIES OF BIOPOLYMER SOLUTIONS

BACKGROUND OF THE INVENTION

1. Field of the Invention

The present invention relates to a method for improving the filterability and injectivity of aqueous solutions of biopolymers used as thickening agents in enhanced oil recovery processes.

2. Description of the Prior Art

The use of water injection or waterflood operations to recover oil from subterranean reservoirs is a well known and commonly employed practice in the petroleum industry. A typical waterflood comprises injecting an aqueous flooding medium, e.g. water, into the reservoir to drive oil through the reservoir toward one or more production wells from which it can be collected at the surface of the earth. Unfortunately, the injected water tends to channel through certain portions of the reservoir. This inability of water to sweep a substantial percentage of the volume of the reservoir within the pattern of the wells employed in the waterflood operation seriously affects the ultimate recovery of oil, and detracts from the ecnomoic attractiveness of the operation. Accordingly, there is a need to improve the sweep efficiency of waterfloods and this need has long been recognized by persons working within the oil industry.

It is taught in the art that poor sweep efficiency is a result of several factors. One is the natural tendency of the liquid to flow in the path of least resistance; hence, water flows through the highly permeable portions of the heterogeneous reservoir more readily than through the less permeable portions. Another factor involves the difference between the mobilities of the injected water and the oil present in the reservoir. In both instances, sweep efficiency of a reservoir can be improved by increasing the viscosity of the injected water.

The use of hydrophilic, viscosity-increasing additives for flood water is known and practiced in the art, and commonly employed additives for this purpose include partially hydrolyzed polyacrylamides, copolymers of acrylamide and acrylates, and one of the very promising groups of thickeners, ionic polysaccharides, particularly the polysaccharide prepared by employing bacteria of the genus Xanthomonas, the most common of which is referred to as polysaccharide B-1459.

While polysaccharides exhibit many advantageous performance characteristics, and are preferred over other hydrophilic polymers in many applications, certain problems have been identified which limit their effectiveness, at least in certain reservoirs. The most effective and desirable polysaccharides from the standpoint of developing high viscosity at relatively low concentration levels, are somewhat difficult to disperse completely in relatively saline environments, e.g. in field brines containing more than about 50,000 parts per million total dissolved solids.

A major problem in using heteropolysaccharides as thickening agents, even after being dispersed into solution, is that the solutions sill exhibit poor injectivity into the reservoir formation. Injectivity impairment is known to be caused by poor dispersion which leads to plugging of the sandface. For this reason, the major manufacturers of heteropolysaccharides advise passing the biopolymer solutions through a series of shear plates to disperse the biopolymer better. For example, in Technical Bulletin XF#5, published by Kelco, a Division of Merck & Co., Inc., a precise specification for shearing a Xanthamonas-type heteropolysaccharide is disclosed.

One approach to solving the problem of poor injectivity in an especially hostile reservoir environment containing water soluble borates is disclosed in U.S. Pat. No. 4,232,739 to Franklin on Nov. 11, 1980. As part of a process for dispersing polysaccharides in brine, a double shearing procedure is advocated. The particular shear conditions in each of the shear steps are those advanced by Kelco, although Kelco does not specify a double shearing procedure. The patent notes that the shear differential pressure across the shear plates should be maintained below the point which causes degradation of the polymer. The resulting polysaccharide solutions are evaluated for injectivity by passing them through a 3 micron filter, although the data are incomplete because the rates at which the solutions pass through the filter are not given.

Another approach is simply to filter or clarify the solution following conventional shearing. While this may give solutions having excellent filterability, the resulting filtrate may not have the requisite viscosity simply because much of the polymer is filtered out. Moreover, such a process is usually time-consuming and wasteful.

A serious problem still exists, therefore, with preparing biopolymer solutions having good reservoir injectivities. In many cases, better injectivities are required than those possible with a solution which passes through a 3 micron filter. Yet, even repeated passes through shear plates do not yield a solution which has the required injectivity and suitable viscosity.

SUMMARY OF THE INVENTION

In accordance with this invention, heteropolysaccharides are more effectively dispersed into an aqueous solution by passing the solution through a colloid mill. The resulting solution is characterized by high filterability through a 47 mm diameter 1.2 micron filter at a constant pressure drop of 40 psi across the filter. The solution exhibits no substantial loss in viscosity following shearing. Because of these properties, solutions prepared according to the present invention have very good injectivities into subterranean formations, and avoid many of the plugging problems which have heretofore existed.

DETAILED DESCRIPTION OF THE INVENTION

The present invention is based, in part, upon the discovery that both the manner of shearing the biopolymer solution and the shear level are of critical importance in obtaining solutions of acceptable injectivities. In particular, passing solutions through shear plates is believed to impose very non-uniform shears on the solutions, inherently incapable of imparting the desired injectivities to the biopolymer solutions. The present invention requires passing the polysaccharide solutions through a colloid or dispersion mill until the solutions readily pass through a 1.2 micron filter. The resulting solutions have no substantial loss in viscosity compared to unsheared solutions. The colloid mill imparts a much more uniform and higher shear stress on the solution, for a longer period of time.

The heteropolysaccharides to which the present invention applies are well characterized in the art. These heteropolysaccharides are produced by the action of bacteria of the genus Xanthomonas upon a variety of carbohydrate substances, including simple sugars such as glucose and fructose, sucrose, and starch. Representative of these bacterial are *Xanthomonas campestris, Xanthomonas phaseoli, Xanthomonas malvacearum, Xanthomonas corotae, Xanthomonas translucens, Xanthomonas hederae* and *Xanthomonas papavericola*. All of the organisms do not produce the heteropolysaccharides with equal effectiveness and hence certain species of the bacteria are more attractive for synthesizing the heteropolymers than are others. *Xanthomonas campestris* is a particularly effective species.

A typical heteropolysaccharide product is that obtained as a result of the action of *Xanthomonas campestris* NRRL B-1459 upon carboyhyrates. This is a polymer containing mannose, glucose, glucuronic acid salts and acetyl radicals in a molar ratio of about 2:1:1:1, respectively. Also present in lesser amounts are about 5.5 weight percent of inorganic materials plus about 0.15 weight percent each of phosphorus and nitrogen. The polysaccharide B-1459 is now a relatively standard product. Its molecular weight is estimated to be in the millions. This polysaccharide is commercially available from a number of sources known to those skilled in the art.

Thickened solutions which have been sheared in accordance with the present invention will have exceptional injectivities making them especially useful for enhanced oil recovery operations. The heteropolysaccharides will generally be present in the solutions to be injected in concentrations ranging between about 0.005 percent and about 1.0 percent by weight. Concentrations in the range between about 0.05 percent and about 0.24 percent are preferred. The exact concentration employed will, of course, depend in part upon the characteristics of the reservoir in which the waterflooding operations is to be carried out and upon the properties of the oil present therein. In general it is preferred that sufficient polymer be employed in the flood water to give the water a viscosity of at least 2 centipoises under reservoir temperature conditions. Concentrations sufficient to give viscosities of about 25 centipoises or higher may advantageously be used.

The heteropolysaccharide concentration in the flood water necessary for effective displacement under a given set of conditions may be readily determined by calculating the mobility ratio for the system at hand. The mobility ratio may be considered to be a measure of the volume of displacing fluid which will be required to reduce the oil content of an oil-bearing reservoir to an ultimate equilibrium value. It is defined by the equation $$MR = \frac{V_o K_w}{V_w K_o}$$

where K designates the reservoir permeability, V represents viscosity and the subscripts w and o denote water and oil respectively. A mobility ratio of unity indicates that the water and the oil will move through the reservoir in the presence of one another with equal ease. A given volume of water at a mobility ratio of less than one will displace a markedly greater volume of oil from a reservoir than will the same amount of water at a mobility ratio greater than one. Where practical, the concentration of the heteropolysaccharide in the flood water should be sufficient to give a mobility ratio less than one. Concentrations between about 0.05 percent and about 0.25 percent by weight are generally effective for this purpose.

The present invention requires the shearing of an aqueous solution of heteropolysaccharide by using a colloid mill. The resulting solution readily passes through a 1.2 micron filter and has a viscosity which is substantially the same as the mixed solution before colloid mill shearing. A particular colloid mill which may be used in the practice of this invention is a Gifford-Wood, Model W 250V, Colloid Mill manufactured by Greerco, Hudson, N.H. 03051. The G-W Colloid Mill is capable of imparting a high degree of energy to the heteropolysaccharide solution through intense forces of impact and hydraulic shear. The amount of particle breakdown can be closely controlled by regulating the clearance between the rotor and the stator of the Mill. Various types of colloid mills (or dispersion mills, as they are sometimes called) may be used in the practice of the invention, including the hammer or turbine type, the smooth-surface disk type, the rough-surface type, and the valve or orifice device. All such colloid mills operate on the principle of creating a fluid stream of high velocity with very great shear forces more uniformly existing with the fluid, which serve to disrupt agglomerates, microgels and other particles in the solution.

The procedures followed in preparing a solution thickened with a heteropolysaccharide for use as a drive water bank following injection of a microemulsion into a reservoir formation in Illinois illustrates the practice of this invention.

EXAMPLE I

A microemulsion prepared according to the conditions outlined in U.S. Pat. No. 4,271,907 (Gale, 6/9/81) and U.S. Pat. No. 4,293,428 (Gale et al, 10/6/81), incorporated by reference, had been injected into the formation. A thickened drive water bank was needed to force the microemulsion and crude oil to a production well. Because the formation had low absolute permeability to gas, ranging between about 20-200 millidarcies, the injectivity of conventionally prepared heteropolysaccharide solutions was unacceptably low, and severe plugging problems were foreseen. An aqueous solution of a heteropolysaccharide was prepared in accordance with the present invention. A volume of about 8400 gallons of an aqueous solution containing about 1400 ppm of Flocon (TM) 4800 (a Xanthangum manufactured by Pfizer, Inc.) and electrolytes was prepared. Electrolytes were added to give the solution better flow characteristics in the formation, which had high level of total dissolved solids (TDS). The electrolytes were present as follows:

| Electrolyte | Concentration (ppm) |
|---|---|
| Sodium | 25,290 |
| Calcium | 1,990 |
| Magnesium | 850 |
| Barium | 44 |
| Chloride | 44,950 |
| Bicarbonate | 99 |
| Ferrous | 8 |

Before shearing, the biopolymer solution had an acceptable visocity of about 40 cp at 11 sec$^{-1}$ measured with a Brookfield viscometer with a UL adaptor. However, its filterability was unacceptable, no more than 200 ml of the solution passing through a 47 mm diameter 1.2 micron Millipore (TM) filter with a 40 psi pressure across the filter before plugging occurred.

The total volume of 8400 gallons was then continuously circulated through the G-W Mill described above for about 6 hours at a flow rate of about 40 gallons/minute. This was sufficient to pass the entire volume through the Mill approximately 2 times. After shearing, 1 liter samples were measured for viscosity and filterability. All samples had a viscosity in the range 38-40 cp at 11 sec$^{-1}$. Most significantly, under the same filter conditions as before, for all samples tested, 1 liter of solution would pass through the 1.2 micron filter in no more than 10 minutes.

In general, sufficient shear will have been achieved with the colloid mill when a sample of a solution of the desired viscosity are capable of meeting certain minimum filterability requirements. This minimum requirement is met for most reservoirs when at least about 600 milliliters of sample is capable of passing through a 47 mm, 1.2 micron filter in no more than 10 minutes. Preferably, 1 liter of solution will pass through the filter in 10 minutes, and most preferably 1 liter in 2 minutes. It should be noted that the exact filterability value needed for good reservoir injectivity will depend upon the formation and sandface permeability, which will of course vary from reservoir to reservoir.

This procedure can be applied to shear biopolymer-containing solutions over a wide range of polymer concentrations ranging from the injection concentration to very concentrated solutions (e.g. broths). Solutions containing the injection composition can be sheared just prior to injection, and for certain process conditions this method is the best application of the invention. Shearing concentrated solutions of biopolymer (1.0 to 4.0 weight percent polymer) can sometimes be beneficial since a higher mass flow rate of active polymer (mass of active polymer/unit time) through the colloid mill can be realized than with a dilute solution. However, as outlined below, there are certain process conditions arising upon dilution of this sheared polymer concentrate that require that the diluted material be sheared again to achieve maximum solution quality (in terms of injectivity). For the range of polymer concentrations for which this invention is contemplated (from less than 100 ppm to over 4 weight percent polymer, to as much as 20 weight percent for broths) this method does not cause a substantial loss of viscosity relative to the solution viscosity prior to shearing.

Occasionally, process conditions require that the polymer in its final diluted state be in solution with certain species that may interact with the polymer or cause polymer/polymer interactions to occur to form microgels (i.e. solutions containing high concentrations of salts, surfactants, or other agents). This is the case in the Examples set forth herein. The solution should be then sheared through the colloid mill after all dilutions are completed. Preferably, the solutions should be injected as soon as practical after being sheared.

The residence time of the polymer solution in the colloid mill that is required to cause good injectivity will depend upon polymer concentration, water salinity, the concentration of other components in solution such as (but not limited to) surfactants, the gap spacing between rotor and stator of the colloid mill, and/or colloid mill type. For a fixed solution composition and colloid mill configuration, the combination of mill gap setting and flow rate are chosen to give the best solution quality. For very stringent injectivity specifications, the solution may have to be recycled through the colloid mill more than once, or passed through a series of colloid mills.

Another example of the improvement in injectivty obtained according to this invention for a particular microemulsion is given below:

EXAMPLE II

An unsheared but thoroughly mixed solution having the following composition was tested for filterability through 5 micron and 1.2 micron millipore (TM) filters (142 mm dia. and 47 mm dia., respectively) with a constant pressure drop across the filter of 40 psi. As noted, filter tests correlate with injectivity into reservoir rocks. The solution was then sheared through a G-W Colloid Mill and retested for filterability.

| Solution Component | Concentration |
| --- | --- |
| xanthan biopolymer | 1000 ppm |
| surfactant (an alkoxylated sulfated primary alcohol) | 2.2 wt. % |
| brine (96,000 ppm TDS) | balance |
| oil (Marcol 70) | 2.8 wt. % |

The results of the test are set forth in the following table:

| Sample | Volume Filtered in Filter Test | Solution Viscosity, cp |
| --- | --- | --- |
| before shearing | 200 ml in 10 minutes (sample plugged filter) | 28 cp |
| after shearing | 1000 ml in 2 minutes (entire 1000 ml sample passed through filter) | 28 cp |

It may be noted that the viscosity of the sample after shearing with the colloid mill was the same as before. However, after shearing, 1000 ml of solution passed through the 1.2 micron filter in 2 minutes whereas before the filter plugged after only 200 ml.

The principle of the invention and the best mode contemplated for applying that principle have been described. It is to be understood that the foregoing is illustrative only and that other means and techniques can be employed without departing from the true scope of the invention defined in the following claims.

I claim:

1. A method for improving the reservoir injectivity of an aqueous heteropolysaccharide solution, said heteropolysaccharide having been produced by the action of bacteria of the genus Xanthomonas upon carbohydrates and present in said solution in a concentration ranging between about 0.005 percent to about 1.0 percent by weight, which comprises shearing said solution, without causing a substantial loss of viscosity to the solution, by passing it through a colloid mill until certain minimum filterability requirements for good reservoir injectivity are met.

2. The method of claim 1 wherein said solution is circulated through said colloid mill until said solution has the characteristic that at least 600 milliliters thereof is capable of passing through a 47 mm diameter 1.2 micron filter in no more than about 10 minutes at a 40 psi pressure drop across the filter.

3. The method of claim 2 wherein at least 1 liter of said solution passes through said filter in no more than about 10 minutes.

4. The method of claim 3 wherein at least 1 liter of said solution passes through said filter in no more than 2 minutes.

5. The method of claim 1 further comprising passing said solution through at least one additional colloid mill.

6. A method for treating an aqueous heteropolysaccharide solution prior to injecting it into a subterranean oil-bearing reservoir, said heteropolysaccharide having been produced by the action of bacteria of the genus Xanthomonas upon carbohydrates and having a concentration in the range of about 0.005 weight percent to about 20 weight percent in said solution, which comprises pumping said solution through a colloid mill until a 600 ml sample thereof is capable of passing through a 47 mm diameter 1.2 micron filter in no more than about 10 minutes at a 40 psi pressure drop across said filter, said solution having a viscosity after shearing which is substantially the same as before shearing.

7. The method of claim 6 wherein said solution is a concentrated broth containing heteropolysaccharide.

8. The method of claim 6 wherein said solution has a heteropolysaccharide concentration in the range 100 ppm to 40,000 ppm.

9. The method of claim 6 wherein said solution additionally contains electrolytes.

10. The method of claim 6 wherein said solution is passed through a series of colloid mills.

11. The method of claim 6 wherein said solution is pumped through said colloid mill until 1 liter of said solution passes through said filter in 10 minutes.

12. The method of claim 10 wherein 1 liter of said solution passes through said filter in 2 minutes.

13. The method of claim 6 wherein said solution is a microemulsion.

14. The method of claim 6 wherein said solution is a concentrated heteropolysaccharide solution.

15. The method of claim 6 wherein said solution has a viscosity of at least 2 centipoise at the temperature of said reservoir both before and after said shearing.

16. An enhanced oil recovery method wherein an aqueous heteropolysaccharide solution is injected into a subterranean formation to drive crude oil to a production well, said heteropolysaccharide having been produced by the action of baceteria of the genus Xanthomonas upon carbohydrates and present in said solution in an amount sufficient to impart a viscosity to the solution of at least 2 centipoise at the temperature of said subterranean formation, which comprises
(a) passing said solution through a colloid mill until a 600 milliliter sample thereof is capable of passing through a 47 mm diameter, 1.2 micron filter in no more than about 10 minutes at a 40 psi pressure drop across said filter, the solution after shearing having a viscosity of at least 2 centipoise at the temperature of said subterranean formation; and
(b) injecting the solution resulting from step (a) into said formation and recovering crude oil from said production well.

17. The method of claim 16 wherein said solution is a microemulsion.

18. The method of claim 16 wherein said solution is a drive water bank.

* * * * *